United States Patent [19]

Klug et al.

[11] Patent Number: 4,753,803

[45] Date of Patent: Jun. 28, 1988

[54] METHOD FOR SIMULTANEOUSLY DRYING AND GRANULATING EXTRACT SUBSTANCES FROM DEPROTEINIZED CALVES BLOOD

[75] Inventors: Otto Klug, Langenpreising, Fed. Rep. of Germany; Heinrich Schlünken, Linz, Austria; Dietmar Siegel, Freising, Fed. Rep. of Germany

[73] Assignee: Hormon-Chemie Munchen GmbH, Munich, Fed. Rep. of Germany

[21] Appl. No.: 913,152

[22] Filed: Sep. 29, 1986

[30] Foreign Application Priority Data

Oct. 4, 1985 [DE] Fed. Rep. of Germany ....... 3535536

[51] Int. Cl.$^4$ ............... A61K 9/00; A61K 15/00; A61K 21/00; B05D 7/00
[52] U.S. Cl. .................. 424/474; 424/475; 424/101; 427/3; 427/213
[58] Field of Search ............ 424/474, 475, 101; 427/3, 213

[56] References Cited

U.S. PATENT DOCUMENTS 3,458,622 7/1969 Hill .................................. 424/468
4,662,880 5/1987 Hamel et al. .................. 514/357 X

FOREIGN PATENT DOCUMENTS 330953 7/1976 Austria .
0106309 4/1984 European Pat. Off. .
1076888 9/1960 Fed. Rep. of Germany .
2143519 5/1974 Fed. Rep. of Germany .
3237303 4/1984 Fed. Rep. of Germany ......... 427/3

OTHER PUBLICATIONS

Schnellen, Med. Welt, vol. 19, No. 3, p. 198, Jan. 1968:–"Uber die Behandlung schlecht heilender Ulzera mit Actihaemyl".
Sucket, H., Fuchs, P., Speiser, P.: Pharmaceutical Technology, Stuttgart, 1978, pp. 409–413.
Ritschel, W. A., The Tablet, Fundamental Principles and Practice of Tableting, Pelletizing and Drugging; Aulendorf in Wuertt., 1966, pp. 211–212, 213.

Primary Examiner—Michael R. Lusignan
Attorney, Agent, or Firm—Mark Dryer

[57] ABSTRACT

The invention relates to a fluidized-bed method for simultaneously obtaining the dry matter from aqueous solutions of extract substances from deproteinized calves blood and producing granules which can be compressed to give solid medicament forms and contain at least 50% by weight of extract substances, relative to the total dry weight of the granules, a binder and pharmaceutically acceptable fillers and carriers, by spraying an aqueous solution of the extract substances and of the binder on to the fillers and carriers and granulating the mixed material at a defined water content in the fluidized bed. After drying, granules ready for compression are obtained, and they are used for producing solid medicament forms of high stability and constant quality.

31 Claims, No Drawings

METHOD FOR SIMULTANEOUSLY DRYING AND GRANULATING EXTRACT SUBSTANCES FROM DEPROTEINIZED CALVES BLOOD

The invention relates to a fluidized-bed method for simultaneously obtaining the dry matter from aqueous solutions of extract substances from deproteinized calves blood and producing granules which can be compressed to give solid medicament forms and contain at least 50% by weight of extract substances, relative to the total dry weight of the granules, and to the use of granules, obtained by this method, for producing pharmaceutical preparations which contain, as the active substance, the extract substances from deproteinized calves blood.

It is known that, in the treatment of slowly healing wounds, extract substances from deproteinized blood of young calves, which substances contain the low-molecular constituents of the calves blood, effect an improvement in the blood flow through the tissue and hence accelerate healing of the wound. Moreover, the extract substances are also used in the case of disorders in cerebral blood flow and metabolism, cf. Schnellen, Med. Welt, volume 19, page 198 (1968). Pharmaceutical preparations which contain such extract substances are commercially available under the name "Actovegin" from Hormonchemie, Munich, or under the label "Actihaemyl" from Solko, Basel.

The extract substances from deproteinized calves blood are extremely heat-sensitive when dry. Prolonged thermal stress above 30° C. produces a brown discoloration which is probably caused by a reaction of glucose with amino acids and peptides (Maillard reaction), a residual water content of more than 4% by weight in the dry matter having a particularly disadvantageous effect and leading to the formation of a brown, viscous mass.

When isolated from calves blood, the extract substances are obtained in aqueous solutions of diverse concentration. German Pat. No. 1,076,888 describes only the production of injectable preparations of a concentration of 30 to 60 mg of dry matter/ml of solution by concentrating solutions of the extract substances. Only gentle drying methods can be considered for obtaining the dry matter, even for the production of solid medicament forms, because of the high thermal instability of the extract substances. Austrian Pat. No. 330,953 has disclosed a method for the production of dry preparations from calves blood extracts, wherein the extract substances are mixed with an adsorbent, for example highly dispersed silica, whereupon the resulting thixotropic gel is dried in vacuo. This method has the disadvantage that accompanying substances, foreign to the extract, must be added to the aqueous solution of the extract substances before drying, since the production of a satisfactory dry substance by this route is not feasible without such additives.

An improved alternative for adsorbing the active substances of blood extracts on solid materials is, according to Austrian Pat. No. 330,953, to obtain the dry matter by freeze-drying (lyophilization) of approximately 5 to 10% aqueous solutions of the extract substances. Apart from the fact that freeze-drying of relatively large volumes of the aqueous solutions consumes a lot of time and energy, freeze-drying has the disadvantage that the lyophilizates obtained represent a very fine and highly hygroscopic powder which is unsuitable for the production of solid medicament forms by direct tabletting or by dry granulation and subsequent compression.

Granules suitable for tabletting have hitherto been produced from the lyophilizate by subsequent moist granulation with polyvinylpyrrolidone as a binder and carboxymethylstarch as a filler, but water cannot be used as the granulating fluid and, instead, organic solvents, for example isopropanol, must be used. Because of their toxicity, however, organic solvents are only used reluctantly for the production of medicament forms which can be administered orally. Moreover, the hygroscopic lyophilizate absorbs moisture from the surrounding air during the granulation process, so that it is necessary either to operate with air-conditioning at a relatively low atmospheric humidity or to subject the finished granules to a drying process at about 40° C. for several hours, the extract substances being exposed to a further temperature stress which adversely affects the quality and leads to a discoloration of the finished preparations on storage.

It is therefore the technical object of the invention to improve both the method for obtaining the dry matter from the aqueous solutions arising in the isolation of the extract substances and the production of granules which can be compressed to give solid medicament forms, while avoiding the abovementioned disadvantages, a uniform improved product quality being an essential requirement in addition to economic advantages. In particular, the dry matter should be obtained under mild conditions during the entire production process and granules ready for compression should be produced with a high weight fraction of extract substances, these granules being processable to give solid medicament forms of high stability, which do not show discolouration even on prolonged storage at ambient temperatures and have more constant quality parameters.

According to the invention, the object is achieved by a method for simultaneously obtaining the dry matter from aqueous solutions of extract substances from deproteinized calves blood and producing granules which can be compressed to give solid medicament forms and contain at least 50% by weight of extract substances, relative to the total dry weight of the granules, a binder and pharmaceutically acceptable fillers and carriers, in a continuous process comprising the steps of:

(a) placing a given quantity of the fillers and carriers into a fluidized-bed granulator and establishing a uniform fluidized bed by introducing a flow of fluidizing gas, (b) spraying a volume, containing the desired quantity of extract substances, of a concentrated aqueous solution of the extract substances, which additionally contains 0.2 to 2 parts by weight of the binder in the dissolved state per 10 parts by weight of extract substances, on to the fillers and carriers in the fluidized bed, the temperature of the fluidizing gas flowing in and the spraying rate being adjusted, during the spraying-in of the total solution volume or at least during the major part thereof, in such a way that, at a fluidized-bed temperature of 25° to 30° C. and at a water content of 15 to 20% by weight in the fluidized bed, the quantity of water sprayed in and that being evaporated approximately correspond to each other, no shapes are formed and the fluidized-bed material remains pulverulent, and (c) agglomerating and granulating the mixed material thus obtained by increasing the water content of the fluidized bed to 35 to 45% by weight, while the solution of the extract substances is still being sprayed in or after completion thereof, until the desired granule size has been reached, and briefly drying the resulting granules at a fluidized-bed temperature of 30° to at most 45° C. by increasing the temperature of the fluidizing gas flowing in.

The advantages of the method according to the invention are, on the one hand, an improvement in the product quality of the granules obtained which, after discharge from the fluidized-bed granulator, can be compressed either directly or after the addition of further pharmaceutically acceptable auxiliaries to give readily storable solid medicament forms of high stability, perfect constant weight and excellent galenic properties. On the other hand, the method according to the invention makes it possible both to obtain the dry matter under mild conditions from large volumes of aqueous solutions of extract substances from deproteinized calves blood and to produce granules ready for compression in a single continuous process in a substantially simpler and more economical manner than has hitherto been the case with the known method.

Commercially available fluidized-bed granulators are suitable for carrying out the method according to the invention. Such fluidized-bed granulators consist essentially of a material container, into which the fluidizing gas flows from the side or from below, both the flow rate and the temperature of the fluidizing gas flowing in being controllable. These devices also have one or more sprayheads in the form of single-component or two-component nozzles, through which pure liquids and solutions can be sprayed into the material container at an adjustable spraying rate by means of a pump and which are arranged such that the atomized liquid or solution flows directly into the fluidized bed. A mechanical agitating or vibrating device on the container floor or a shaking device are intended to provide an additional mixing effect if required.

For carrying out the method in practice, a given quantity of the fillers and carriers, which depends on the desired weight proportion of these additives in the finished granules and, in the method according to the invention, is in every case less than 50% by weight, preferably 25 to 45% by weight, relative to the total dry weight of the finished granules, is placed into the material container and a uniform fluidized bed is formed by introducing the flow of fluidizing gas. Galenically conventional fillers and carriers of small particle size, which at the same time have a large surface area and are insoluble or only sparingly soluble in water, are above all suitable for producing the granules according to the invention. As examples of suitable fillers and carriers having the properties described above, microcrystalline cellulose (commercially available, for example, under the name Avicel PH 101), cross-linked sodium carboxymethylcellulose (commercially available, for example, under the name Ac-Di-Sol), cross-linked polyvinylpyrrolidone (commercially available, for example, under the name Polyplasdone) or mixtures of these substances may be mentioned, and the mixing ratios can be selected as desired within a wide range and, here again, mixtures of equal parts by weight of these substances are preferred. Microcrystalline cellulose or cross-linked sodium carboxymethylcellulose have proven to be very particularly suitable for this purpose.

As the fluidizing gas, dry air can be used in a very simple manner without any disadvantage regarding the quality and stability of the extract substances. However, other gases which are inert towards the extract substances such as, for example, nitrogen, are of course also suitable for forming the fluidized bed. The total throughput of fluidizing gas per hour depends on the size of the fluidized-bed granulator and amounts to, for example, 500–3000 m$^3$/h for a nominal volume of the material container of 60 liters. As soon as a uniform fluidized bed has formed due to the flow pressure, spraying of the aqueous solution of the extract substances can be started. For this purpose, concentrated aqueous solutions are advantageously used which contain up to 50% by weight, preferably 15 to 25% by weight, of extract substances and the volumes of which are calculated such that the total quantity of the extract substances sprayed on is at least 50% by weight, preferably 55–70% by weight, relative to the total dry weight of the finished granules.

These solutions additionally contain 0.2 to 2 parts by weight of a water-soluble binder, preferably 0.5 to 1 part by weight, per 10 parts by weight of extract substances. The weight proportion of the binder in the finished granules is then, for example 1 to 10% by weight, preferably 2 to 6% by weight, relative to the total dry weight of the granules.

Suitable binders for producing the granules according to the invention are galenically conventional water-soluble binders, for example pregelatinized starch, water-soluble cellulose, such as methylcellulose, hydroxypropylcellulose, hydroxypropylmethylcellulose or other water-soluble high-molecular compounds such as polyvinyl alcohol, polyvinylpyrrolidone and the like. Polymers of 1-vinyl-2-pyrrolidone, which are commercially available, for example, under the name Kollidon K 25 or Kollidon 90, are used with particular preference.

The temperature of the fluidizing gas flowing in during the spraying process and the spraying rate, at which the aqueous solution of the extract substances is sprayed together with the binder on to the fluidized fillers and carriers, depends on the quantity of the auxiliaries originally introduced and on the nominal volume of the material container of the fluidized-bed granulator. In this phase of the method, the temperature and the spraying rate are matched such that, at a fluidized-bed temperature of 25° to 30° C., a steady water content of 15 to 20% by weight, relative to the total weight, is established in the fluidized-bed material and the quantity of water sprayed in and that being evaporated approximately correspond to each other.

For this purpose, fluidizing gas temperatures of about 30° to 80° C. are required, depending on the quantity of the fillers and carriers introduced and on the size of the material container.

Under the conditions indicated, shaping does not yet take place. The fillers and carriers remain capable of absorbing the extract substances which are advantageously not subjected to any significant temperature stress in the fluidized bed, while the major part of the water is removed, and a fine flowable mixed material is obtained which remains pulverulent in this first phase of the method and hardly tends to agglomerate.

The agglomeration of the pulverulent material for building up the granules to the desired size is obtained in the method according to the invention by increasing the water content in the fluidized bed to 35 to 45% by weight, preferably to 38 to 40% by weight. For this purpose, the water content can be increased either during the spraying process itself, when the major part of the desired quantity of extract substances has already been sprayed on, or when spraying-on of the extract substances has been completed. In a particularly advantageous embodiment of the method, the major part of the solution, which contains the extract substances and the binder, for example 75 to 85% by volume, depending on the concentration of extract substances, of the total volume of the solution to be sprayed on, is sprayed on under the conditions which are indicated above and which do not lead to agglomeration of the mixed material, whereas, while the remaining part of the solution volume is sprayed on, the temperature of the fluidizing gas flowing in is lowered and/or the spraying rate is increased, so that a greater quantity of water is sprayed in than can be evaporated simultaneously and, consequently, the water content of the fluidized bed rises to the value required for agglomerating and granulating.

It is also possible, however, to spray on the total solution volume under conditions which do not lead to agglomeration, and then to increase the water content in the fluidized bed to the value required for granulation by spraying in pure water.

As soon as the water content in the fluidized bed exceeds a value of about 35% by weight, agglomeration starts and even, uniform granules are produced.

During the entire granulation step, a water content within the limits indicated above is maintained in the fluidized-bed material. Depending on the adjustment of the water content, granules which have a diameter in the range from 0.03 to 2 mm, preferably 0.05 to 1 mm, can be obtained reproducibly by the method according to the invention.

When granules of the desired size have formed, the drying phase is started by raising the temperature of the fluidizing gas. The temperature of the fluidizing gas is here advantageously selected such that, for mild treatment of the extract substances, the granule temperature in the fluidized bed does not exceed 30° to 32° C. Drying is finished as soon as the granule temperature rises. To remove the residual water, the temperature of the granules can be allowed to rise for a short period, for example 5 to 15 minutes, to 40° to 45° C., advantageously 40° to 43° C., without adversely affecting the stability of the extract substances and the quality of the granules. In this way, granules with a maximum water content of about 1.5 to 3% by weight, relative to the total weight, are obtained.

The method according to the invention is efficient, simple and easily reproducible. The production of 58 kg of dry granules, ready for compression, from the aqueous concentrate of the extract substances from deproteinized calves blood takes, for example, only about 7 hours in continuous operation, whereas freeze-drying of the same quantity, carried out according to the state of the art, alone takes about 7 to 9 days.

The granules produced according to the invention have a high weight proportion of extract substances and, at uniform particle size, show excellent flow behavior, which allows them to be processed into solid medicament forms at perfect constant weight and high stability. The invention therefore also relates to the use of the granules according to the invention for producing solid medicament forms which contain extract substances from deproteinized calves blood as the active substance. Preferably, compressed items, such as tablets, coated tablets, tablet cores or other compressed products of any desired shape and size, are produced.

The granules produced according to the invention can here be compressed directly or after the admixture of further auxiliaries known in galenics, such as tablet binders, fillers, preservatives, tablet-disintegrating agents and the like. The nature and quantity of these auxiliaries depends on the desired mechanical strength and the dissolution rate of the compressed product.

Suitable examples of such auxiliaries for admixing before compression are stearates, such as magnesium stearate, calcium stearate and the like, or other lubricants conventionally used in tabletting, for example talc or glycerol esters of saturated natural fatty acids, such as are commercially available, for example, under the name Precirol, in a quantity of 1 to 10% by weight, relative to the total weight of the finished preparation.

The finished preparations contain, for example, 150 to 250 mg of extract substances per dose unit, at a total weight of the tablet or tablet core of 300 to 500 mg.

Solid medicament forms, produced with the use of the granules according to the invention, do not show any discoloration even on prolonged storage at room temperature and have more constant quality parameters.

The examples which follow illustrate the invention in more detail:

(a) Production of the Granules

EXAMPLE 1

3000 g of a mixture of equal parts by weight of Avicel PH 101 (microcrystalline cellulose) and Polyplasdone (cross-linked polyvinylpyrrolidone) are placed into the material container of a fluidized-bed granulator having a nominal volume of 7 liters, and a uniform fluidized bed is formed by introducing a flow of dry air at a flow rate of 500 m³ per hour and a temperature of 80° C.

20 Liters of a 20% aqueous solution of the extract substances are mixed with 1 liter of 20% aqueous Kollidon solution, fed by means of a peristaltic pump to a two-component nozzle and sprayed into the fluidized bed. The spray rate is controlled such that a fluidized-bed temperature of 28° to 30° C. and a steady water content of the fluidized-bed material of about 15% by weight are established in the fluidized-bed granulator, the quantity of water sprayed in and that being evaporated being in balance and no agglomeration being observable.

The mean spray rate for maintaining these conditions is 70 g of solution per minute. After about ¾ of the total solution volume have been sprayed in, the temperature of the inlet air is lowered to 30° C. and the remainder of the solution volume is sprayed in at the same spray rate. The steady water content in the fluidized bed then rises and the agglomeration of the powder starts at a water content of 38 to 40% by weight. Granulation is continued at this water content until granules of a diameter from 0.06 mm to 0.8 mm have formed from the total powder quantity. After completion of spraying, the temperature of the inlet air is raised again to 60°–80° C. and the drying phase is thus initiated. The temperature of the granules during drying is 30° to 32° C. Drying is complete when the temperature of the granules rises. To remove the residual water, the temperature of the granules is held for 15 minutes at 43° C. This gives 7350 g of granules having the following properties

| | |
|---|---|
| Content of extract substances | 544.2 mg/g of granules |
| Kollidon K 25 | 27.3 mg/g of granules |

| | |
|---|---|
| Avicel PH 101 | 204.0 mg/g of granules |
| Polyplasdone | 204.0 mg/g of granules |
| Residual water content | about 20 mg/g of granules, corresponding to about 2% |
| Diameter | from 0.08 to 0.8 mm |

EXAMPLE 2

Experiment 1 is repeated, 3000 g of microcrystalline cellulose (Avicel PH 101) being used as the filler or carrier and 1 liter of a 20% aqueous solution of Kollidon 90, 1-vinyl-2-pyrrolidone polymer, being added as the binder for the solution of the extract substances.

This gives granules having the following properties:

| | |
|---|---|
| Content of extract substances | 544.2 mg/g of granules |
| Kollidon 90 | 27.3 mg/g of granules |
| Avicel PH 101 | 408 mg/g of granules |
| Residual water content | about 20 mg/g of granules, corresponding to about 2% |
| Diameter | from 0.08 to 0.8 mm |

EXAMPLE 3

15,000 g of Avicel PH 101 (microcrystalline cellulose) and 10,000 g AC-DI-Sol (cross-linked sodium carboxymethylcellulose) are placed into the material container of a fluidized-bed granulator having a nominal volume of 60 liters. A uniform fluidized bed is maintained by introducing air at a flow rate of 800 m$^3$/hour and at a temperature of 80° C. 166.6 Liters of a 20% aqueous solution of the extract substances are mixed with a solution of 1660 g of Kollidon K 25 in 16.6 liters of water, fed in by means of a peristaltic pump (3 nozzles having a 1.2 mm nozzle orifice) and sprayed into the fluidized bed. At a spray rate of about 600 g of Actovegin/Kollidon solution per minute, a steady water content of about 15% and a temperature of 30° to 32° C. are established in the fluidized bed.

After 140 liters have been sprayed in under these conditions, the inlet air temperature is lowered to room temperature, and the water content is thus increased and the agglomeration phase is initiated. After completion of spraying-in, the granules formed in the fluidized-bed granulator are dried at an inlet air temperature of 80° C.

The dried granules have the following properties:

| | |
|---|---|
| Bulk density | 0.53 g/cm$^3$ |
| Tamped density | 0.63 g/cm$^3$ |
| Flowability | 12.30 g/cm$^2$ second |
| Water content | 1.6% |
| Particle size | 60–500 μm |

EXAMPLE 4

22,000 g Microcrystalline cellulose (Avicel PH 101) are placed into the material container of a fluidized-bed granulator having a nominal volume of 60 liters. A uniform fluidized bed is maintained by introducing air at a flow rate of 800 m$^3$/hour and at a temperature of 70° C. 166.6 Liters of 20% aqueous solution of Actovegin (extract substances from deproteinized calves blood) are mixed with a solution of 1660 g of Kollidon 90 (polymer of 1-vinyl-2pyrrolidone) in 16.6 liters of water, fed in by means of a peristaltic pump (3 nozzles having a 1.2 mm nozzle orifice) and sprayed into the fluidized bed. At an initial spray rate of about 600 g of Actovegin/Kollidon 90 solution per minute, a steady water content of about 15% and a temperature of 30°–32° C. are established in the fluidized bed.

After 2.5 hours at the same inlet air temperature, the spray rate is increased to 900 g/minute and the agglomeration phase is intensified. After the end of spraying-in, the granules formed are dried in the fluidized-bed granulator at an inlet air temperature of 70° C.

The dried granules have the following properties:

| | |
|---|---|
| Bulk density | 0.53 g/cm$^3$ |
| Tamped density | 0.63 g/cm$^3$ |
| Flowability | 12.30 g/cm$^2$ second |
| Water content | 1.6% |
| Particle size | 60–500 μm |

(b) Use of the Granules for Producing Solid Medicament Forms

EXAMPLE 5

Tablet cores 7200 g of granules obtained according to Example 1 are mixed with 60 g of magnesium stearate and 40 g of talc and compressed in a rotary pelletting machine under a pressing power of 78.5–150 N/mm$^2$ to give tablet cores of 365 mg weight. This gives tablet cores having the following properties:

| Core properties: | | Composition: | |
|---|---|---|---|
| Diameter | 10.0 mm | Extract substances | 200 mg |
| Thickness | 5.5 mm | Polyplasdone | 75 mg |
| Breaking strength | 115 N | Avicel PH 101 | 75 mg |
| Attrition (4 min) | 20.1% | Kollidon K 25 | 10 mg |
| Disintegration | 8–10 min | Talc | 2 mg |
| | | Mg stearate | 3 mg |

These tablet cores have a constant content of extract substances and show no deterioration in quality or discoloration when stored for 24 months at room temperature.

EXAMPLE 6

Tablets 7200 g of granules obtained according to Example 1 are mixed with 60 g of magnesium stearate and 40 g of talc and compressed in a rotary pelletting machine under a pressing power of 98.1 to 196.2 N/mm$^2$ to give tablets of 730 mg weight. This gives tablets having the following properties:

| Tablet properties: | | Composition: | |
|---|---|---|---|
| Oblong tablet | | Extract substances | 400 mg |
| Length | 18 mm | Polyplasdone | 150 mg |
| Width | 7 mm | Avicel PH 101 | 150 mg |
| Thickness | 6.7 mm | Kollidon K 25 | 20 mg |
| Breaking strength | 180 N | Talc | 4 mg |
| Attrition (4 min) | 0.1% | Mg stearate | 6 mg |
| Disintegration | 10 minutes | | |

What we claim is:

1. A method for simultaneously obtaining the dry matter from aqueous solutions of extract substances from deproteinized calves blood and producing granules which can be compressed to give solid medicament forms and contain at least 50% by weight of extract substances, relative to the total dry weight of the granules, a binder and pharmaceutically acceptable fillers and carriers, in a continuous process comprising the steps of:
  (a) placing a given quantity of the fillers and carriers into a fluidized-bed granulator and establishing a uniform fluidized bed by introducing a flow of fluidizing gas,
  (b) spraying a volume, containing the desired quantity of extract substances, of a concentrated aqueous solution of the extract substances, which additionally contains 0.2 to 2 parts by weight of the binder in the dissolved state per 10 parts by weight of extract substances, on to the fillers and carriers in the fluidized bed, the temperature of the fluidizing gas flowing in and the spraying rate being adjusted, during the spraying-in of the total solution volume or at least during the major part thereof, in such a way that, at a fluidized-bed temperature of 25° to 30° C. and at a water content of 15 to 20% by weight in the fluidized bed, the quantity of water sprayed in and that being evaporated approximately correspond to each other, no shapes are formed and the fluidized-bed material remains pulverulent, and
  (c) agglomerating and granulating the mixed material thus obtained by increasing the water content of the fluidized bed to 35 to 45% by weight, while the solution of the extract substances is still being sprayed in or after completion thereof, until the desired granule size has been reached, and briefly drying the resulting granules at a fluidized-bed temperature of 30° up to at most 45° C. by increasing the temperature of the fluidizing gas flowing in.

2. The method as claimed in claim 1, wherein 25 to 45% by weight of fillers and carriers, relative to the total dry weight of the granules, are placed into the fluidized-bed granulator.

3. The method as claimed in claim 1, wherein the fillers and carriers are microcrystalline cellulose or cross-linked sodium carboxymethylcellulose.

4. The method as claimed in claim 1, wherein the fillers and carriers are a mixture of equal parts of microcrystalline cellulose and cross-linked polyvinylpyrrolidone.

5. The method as claimed in claim 1, wherein the fluidizing gas is air.

6. The method as claimed in claim 1, wherein the solution sprayed on contains 15 to 25% by weight of extract substances.

7. The method as claimed in claim 1, wherein the solution sprayed on contains 0.5 to 1 part by weight of binder per 10 parts by weight of extract substances.

8. The method as claimed in claim 1, wherein the binder is a polymer of 1-vinyl-2-pyrrolidone.

9. The method as claimed in claim 1, wherein, after the major part of the solution volume containing the extract substances and the binder has been sprayed on, the water content of the fluidized bed is raised, for the agglomeration and granulation, by lowering the temperature of the fluidizing gas flowing in.

10. The method as claimed in claim 1, wherein, after the major part of the solution volume containing the extract substances and the binder has been sprayed on, the water content of the fluidized bed is raised, for the agglomeration and granulation, by increasing the spraying rate.

11. The method as claimed in claim 1, wherein, after spraying-on of the solution volume containing the extract substances and the binder has been completed, the water content of the fluidized bed is raised, for the agglomeration and granulation, by spraying in pure water.

12. The method as claimed in claim 1, wherein the water content of the fluidized bed is increased to 38 to 40% by weight for the agglomeration and granulation.

13. The method as claimed in claim 1, wherein the granules formed are dried at a fluidized-bed temperature of 30° to 35° C. and the residual water content is removed by briefly raising the temperature to 40°-45° C.

14. The method as claimed in claim 1, wherein the finished granules contain 53 to 70% by weight of extract substances, relative to the total dry weight of the granules.

15. The method as claimed in claim 1, wherein the finished granules have a diameter in the range from 0.05 to 1 mm.

16. A method for producing pharmaceutical preparations of extract substances from deproteinized calves blood by simultaneously obtaining the dry matter and granules which can be compressed to give solid medicament forms and contain at least 50% by weight of extract substances, a binder and pharmaceutically acceptable fillers and carriers, from aqueous solutions of the extract substances in a continuous process comprising the steps of:
  (a) placing a given quantity of the fillers and carriers into a fluidized-bed granulator and establishing a uniform fluidized bed by introducing a flow of fluidizing gas,
  (b) spraying a volume, containing the desired quantity of extract substances, of a concentrated aqueous solution of the extract substances, which additionally contains 0.2 to 2 parts by weight of the binder in the dissolved state per 10 parts by weight of extract substances, on to the fillers and carriers in the fluidized bed, the temperature of the fluidizing gas flowing in and the spraying rate being adjusted, during the spraying-in of the total solution volume or at least during the major part thereof, in such a way that, at a fluidized-bed temperature of 25° to 30° C. and at a water content of 15 to 20% by weight in the fluidized bed, the quantity of water sprayed in and that being evaporated approximately correspond to each other, no shapes are formed and the fluidized-bed material remains pulverulent,
  (c) agglomerating and granulating the mixed material thus obtained by increasing the water content of the fluidized bed to 35 to 45% by weight, while the solution of the extract substances is still being sprayed in or after completion thereof, until the desired granule size has been reached, and briefly drying the resulting granules at a fluidized-bed temperature of 30° up to at most 45° C. by increasing the temperature of the fluidizing gas flow-in and
  (d) compressing the dry granules to give tablets, coated tablets, or tablet cores.

17. The method as claimed in claim 16, wherein 25 to 45% by weight of fillers and carriers, relative to the total dry weight of the granules, are placed into the fluidized-bed granulator.

18. The method as claimed in claim 16, wherein the fillers and carriers are microcrystalline cellulose or cross-linked sodium carboxymethylcellulose.

19. The method as claimed in claim 16, wherein the fillers and carriers are a mixture of equal parts of microcrystalline cellulose and cross-linked polyvinylpyrrolidone.

20. The method as claimed in claim 16, wherein the fluidizing gas is air.

21. The method as claimed in claim 16, wherein the solution sprayed on contains 15 to 25% by weight of extract substances.

22. The method as claimed in claim 16, wherein the solution sprayed on contains 0.5 to 1 part by weight of binder per 10 parts by weight of extract substances.

23. The method as claimed in claim 16, wherein the binder is a polymer of 1-vinyl-2-pyrrolidone.

24. The method as claimed in claim 16, wherein, after the major part of the solution volume containing the extract substances and the binder has been sprayed on, the water content of the fluidized bed is raised, for the agglomeration and granulation, by lowering the temperature of the fluidizing gas flowing in.

25. The method as claimed in claim 16, wherein, after the major part of the solution volume containing the extract substances and the binder has been sprayed on, the water content of the fluidized bed is raised, for the agglomeration and granulation, by increasing the spraying rate.

26. The method as claimed in claim 16, wherein, after spraying-on of the solution volume containing the extract substances and the binder has been completed, the water content of the fluidized bed is raised, for the agglomeration and granulation, by spraying in pure water.

27. The method as claimed in claim 16, wherein the water content of the fluidized bed is increased to 38 to 40% by weight for agglomeration and granulation.

28. The method as claimed in claim 16, wherein the granules formed are dried at a fluidized-bed temperature of 30° to 35° C. and the residual water content is removed by briefly raising the temperature to 40°–45° C.

29. The method as claimed in claim 16, wherein the finished granules contain 53 to 70% by weight of extract substances, relative to the total dry weight of the granules.

30. The method as claimed in claim 16, wherein the finished granules have a diameter in the range from 0.05 to 1 mm.

31. The method as claimed in claim 16, wherein the dry granules are mixed with pharmaceutically acceptable additives selected from the group consisting of fillers, preservatives, aroma substances and tablet binders and the mixture obtained is compressed to give tablets, coated tablets or tablet cores.

* * * * *